United States Patent
Palumbo et al.

[11] Patent Number: 5,899,894
[45] Date of Patent: May 4, 1999

[54] ABSORBENT ARTICLE WITH ELASTICATED FLAPS

[75] Inventors: Gianfranco Palumbo; Remo Di Girolamo, both of Pescara, Italy

[73] Assignee: Societa' Consortile Ricerche Angelini, S.p.A., Pescara, Italy

[21] Appl. No.: 08/884,070

[22] Filed: Jun. 27, 1997

Related U.S. Application Data

[62] Continuation of application No. 08/516,358, Aug. 17, 1995, abandoned, which is a continuation of application No. 08/190,061, filed as application No. PCT/EP92/01708, Jul. 28, 1992, abandoned.

[30] Foreign Application Priority Data

Jul. 30, 1991 [IT] Italy .................................. TO91A0605

[51] Int. Cl.⁶ ..................................................... A61F 13/16
[52] U.S. Cl. ........................ 604/378; 604/383; 604/385.2
[58] Field of Search .................................... 604/358, 383, 604/381, 382, 385.1–387, 378

[56] References Cited

U.S. PATENT DOCUMENTS

| | | | |
|---|---|---|---|
| 2,969,065 | 1/1961 | Fainsworth | 604/385.2 |
| 4,184,902 | 1/1980 | Karami | 604/383 |
| 4,695,278 | 9/1987 | Lawson . | |
| 4,743,246 | 5/1988 | Lawson | 604/385.2 |
| 4,780,352 | 10/1988 | Palumbo | 604/372 |
| 4,808,177 | 2/1989 | Des Marais et al. | 604/385.2 |
| 4,892,528 | 1/1990 | Suzuki et al. | 604/385.2 |
| 5,037,409 | 8/1991 | Chen et al. | 604/358 |
| 5,080,658 | 1/1992 | Igaue et al. | 604/385.2 |
| 5,167,653 | 12/1992 | Igaue et al. | 604/385.2 |

FOREIGN PATENT DOCUMENTS

| | | |
|---|---|---|
| 0207904 | 1/1987 | European Pat. Off. . |
| 0228821 | 7/1987 | European Pat. Off. . |
| 0243013 | 10/1987 | European Pat. Off. . |
| 0251332 | 1/1988 | European Pat. Off. . |
| 0346477 | 12/1989 | European Pat. Off. . |
| 391476 | 10/1990 | European Pat. Off. ............ 604/385.1 |
| 0422504 | 4/1991 | European Pat. Off. . |
| 3038535 | 6/1982 | Germany . |
| 2142564 | 5/1990 | Japan . |
| 2103933 | 3/1983 | United Kingdom . |
| 2263622 | 8/1993 | United Kingdom ................ 604/385.2 |
| 8909549 | 10/1989 | WIPO . |
| WO 9014813 | 5/1990 | WIPO . |

*Primary Examiner*—Mark O. Polutta
*Attorney, Agent, or Firm*—Sughrue, Mion, Zinn, Macpeak & Seas, PLLC

[57] ABSTRACT

A disposable absorbent article such as a diaper is provided with a continuous upper layer, an absorbent element, an impermeable plastics sheet, elastic parts positioned along the lateral edges to either side of the absorbent element and two elasticized flaps positioned inwardly of the elastic parts. Each flap is formed out of the continuous upper layer by use of an elastic element fixed along its entire length to the inner surface of the continuous layer. The continuous upper layer is liquid-permeable in the zone between the two elastic elements of the flaps and impermeable in the two adjacent zones located between the elastic elements and the lateral edges of the absorbent article. In use, the elastic elements contract, lifting the continuous upper layer off the underlying surface, at least at the crotch area, forming two longitudinal barriers which are impermeable on the side facing the lateral edges of the absorbent article, thus ensuring a more efficient containment of lateral leakage of liquids and solids in an absorbent article of simplified structure.

11 Claims, 3 Drawing Sheets

ABSORBENT ARTICLE WITH ELASTICATED FLAPS

This is a continuation of application Ser. No. 08/516,358 filed Aug. 17, 1995, abandoned, which is a continuation of application Ser. No. 08/190,061 filed Jan. 31, 1994 and now abandoned, which is a 371 of Ser. No. PCT/GP 92/01708 filed Jul. 28, 1992.

BACKGROUND OF THE INVENTION

The present invention relates to disposable absorbent articles such as, for example, diapers for infants or incontinent adults and relates more specifically to absorbent articles of simplified structure having seal elements at the crotch with an improved ability to contain lateral leaks.

Disposable absorbent articles such as diapers for infants or incontinent adults, designed to absorb and retain body fluids, are well known and generally consist of an upper layer of non-woven fabric permeable to liquids and designed to be in contact with the user's skin, an impermeable plastics sheet and an element of absorbent material, commonly known as a pad, between the two said layers.

One problem linked to the use of such absorbent articles is the containment of leakage at the crotch through the lateral edges which, in use, are positioned round the user's legs.

The use along the lateral edges of the absorbent article of elastic elements designed to provide, in use, a seal round the user's legs, has been known for some time, as shown in U.S. Pat. No. 3,860,003.

To improve the seal along the lateral edges, especially the containment of solid excrement which, by its nature, is not absorbed by the pad but tends to remain on the surface of the upper permeable layer, it has been proposed, as an alternative to or in combination with the conventional elastic elements along the lateral edges, to adopt elasticated flaps positioned inside the lateral edges of the absorbent article and either at the two sides of the pad or above it.

In use, the flaps are lifted from the surface of the absorbent article by the elastic elements incorporated in the said flaps, forming two longitudinal barriers able to guarantee better containment of lateral leakage.

For example, U.S. Pat. No. 4,704,116 describes a diaper of conventional structure with elasticated lateral edges and provided with two flaps positioned longitudinally, inwardly of these edges, above the pad, each flap in turn being delimited by two longitudinal edges and two ends.

Each flap is fixed to the upper layer of non-woven fabric along its outer longitudinal edge and at both ends, and is provided with at least one elastic element along the longitudinal edge facing the centre of the diaper.

The flaps are permeable to liquids and can either be formed by appropriately folding the upper non-woven fabric layer itself, or made separately and applied to the said upper layer.

This type of construction gives better protection against lateral leakage at the crotch but involves using more material to form the elasticated flaps.

In addition, as is commonly known in the art, if these flaps are to be impermeable to liquids, it is necessary for example that they be separately made of an impermeable material different from the material forming the upper permeable layer of the absorbent article; or, in the case of flaps made by folding the upper layer of non-woven fabric itself, it is necessary appropriately to treat the fabric or to add further impermeable elements.

A further development is presented in U.S. Pat. No. 4,808,177 which describes an absorbent article provided with the conventional elastics along the lateral edges to seal round the user's legs and with two so-called "floating" elasticated flaps positioned inwards of the said elasticated edges and characterized by a simplified structure.

In this patent each "floating" flap is made with an elastic element positioned longitudinally between the absorbent pad and the upper permeable non-woven fabric layer: the elastic element is fixed at both ends to the upper surface of the pad and to the lower surface of the non-woven fabric layer, while the intermediate portion remains unattached to the layers surrounding it.

In use the two elastic elements, contracting at the unattached intermediate portion, lift the upper layer at either side of the pad forming two longitudinal barriers.

Although this arrangement provides an absorbent article with simply constructed elasticated flaps, there is a need for an absorbent article with improved containment of lateral leakage characterised by impermeable elasticated flaps of simple structure whose manufacture does not involve a significantly larger use of raw material or the use of further treatment of materials compared to an absorbent article without elasticated flaps.

SUMMARY OF THE INVENTION

The object of the present invention is to improve the containment of lateral leakage of liquids and solid excrement in disposable absorbent articles.

The present invention is directed to a new and improved absorbent article provided with elasticated lateral edges and with two impermeable elasticated flaps of simple structure formed by a continuous upper layer which is permeable to liquids in the central portion positioned along the longitudinal axis by impermeable in the two adjoining portions facing the lateral edges of the absorbent article.

BRIEF DESCRIPTION OF THE DRAWINGS

Additional characteristics and advantages of the invention will become apparent from the following description, given as a non-limitative example, with reference to the appended drawings, in which.

DETAILED DESCRIPTION OF THE INVENTION

The absorbent articles of the present invention will be described here with reference to their use as disposable absorbent articles; these articles are worn by the users in direct contact with the body, for the purpose of absorbing body fluids, and are subsequently thrown away after a single use.

Figure 1:
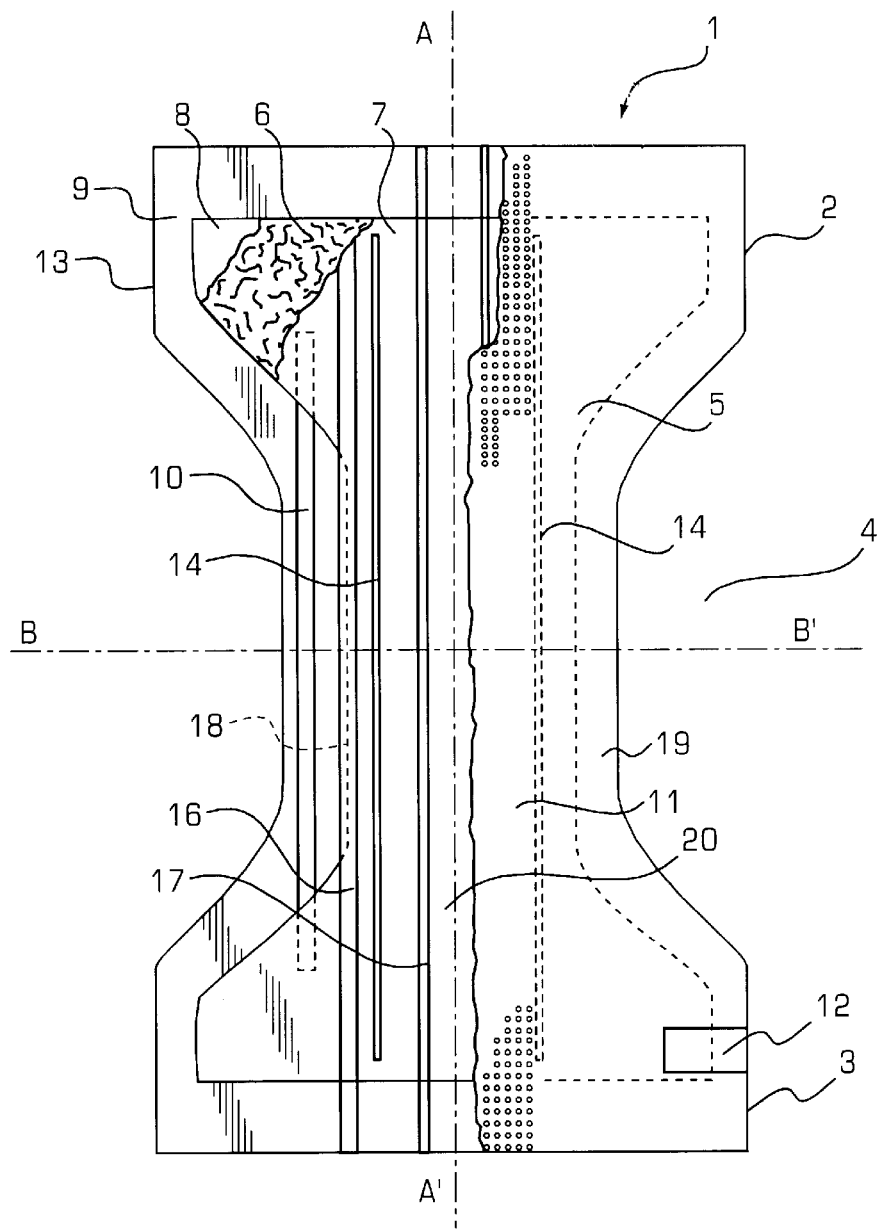
FIG. 1 is a plan view of a disposable diaper according to the present invention.

The disposable diaper shown in FIG. 1 is a preferred embodiment of an absorbent article according to the present invention, but it is understood that the invention is applicable to other disposable absorbent articles, such as articles for incontinent people and the like.

FIG. 1 is a plan view of a diaper 1 spread flat, with a few portions of the structure sectioned to show the structure of the diaper more clearly; in particular the view shows the side of the diaper which comes into contact with the user.

FIG. 1 shows two outermost regions, a front region 2 and a rear region 3, which in use are positioned round the user's waist, and a central region 4 between them which, in use, is positioned about at the crotch; it also shows a longitudinal axis AA' and a transverse axis BB'.

The diaper includes a continuous single sheet upper layer 5, provided for direct contact with the user's skin, an absorbent element 6 positioned between two tissue layers 7, 8, preferably of the wet-strength type, an impermeable plastics sheet 9, elastic elements 10 positioned at either side of the absorbent element 6 along the lateral edges of the diaper and provided to ensure, in use, a seal round the user's legs, and two elasticated flaps 11 made according to the present invention. Also visible in the rear region 3 is one of the two adhesive tabs 12 commonly used to fix the diaper around the user's waist.

The continuous upper layer 5 and the plastics sheet 9 have the same shape and dimensions, following the outline 13 of the whole diaper.

The elasticated flaps 11, symmetrical relative to the axis AA', are positioned longitudinally along the lateral edges of the diaper, inwardly of the elastic elements 10. In the configuration illustrated the flaps 11 are parallel to the axis AA'.

Each flap 11 includes an elastic element 14 positioned under the continuous upper layer 5 and parallel to the longitudinal axis AA', which extends for substantially the entire length of the absorbent element 6.

The elastic elements 14 are fixed under tension along substantially the entire length of the inner surface of the continuous upper layer 5 by fixing lines 15 formed for example by adhesive.

Each flap 11 also includes an outer seal line 16 and an inner seal line 17, both provided with adhesive for example, which join the continuous upper layer 5 to the underlying elements of the absorbent article and are positioned on either side of each elastic element 14, preferably parallel to this latter.

The outer and inner seal lines, 16 and 17, extend along the entire length of the diaper 1 and therefore together join between themselves the inner surface of the continuous upper layer 5 to the upper surface of the immediately underlying layer, which can be either the tissue layer 7 covering the absorbent element 6 or the impermeable plastics sheet 9.

The outer seal line 16 is positioned between the elastic element 10 along the lateral edge of the diaper and the elastic element 14 of the flap 11, for example between the elastic element 10 and the longitudinal edge 18 of the absorbent element 6, at least in the central region 4 of the diaper where the absorbent element 6 is characterised by a narrower width than at the front region 2 or rear region 3.

In the illustrated configuration the outer seal line 16 is positioned so that it is superimposed on the longitudinal edge 18 of the absorbent element 6 at the central region 4 of the diaper and is wide enough to ensure that along the said edge 18 the continuous upper layer 5 is fixed at the same time to the upper surface of the tissue layer 7 and to the impermeable plastics sheet 9.

The inner seal line 17 is positioned between the elastic element 14 of the flap 11 and the longitudinal axis AA' of the diaper 1; in particular the two elasticated flaps 11 can share a single inner seal line 17.

As shown in FIG. 1, on the upper surface of the diaper 1, that is on the outer surface of the continuous upper layer 5, there are two lateral zones 19 outwardly of the two elastic elements 14 and a central zone 20 between the said two elastic elements 14.

Figure 2:
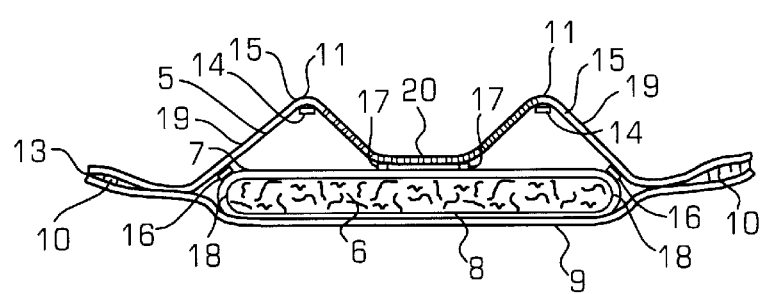
FIG. 2 is a sectional view along the axis BB' of the diaper of FIG. 1 with the elasticated flaps lifted.

In an entirely known way, in use the elastic elements 14 of the flaps 11 contract lifting the continuous upper layer 5 to form two raised barriers extending longitudinally along the sides of the absorbent element 6, as shown in FIG. 2; the side of each barrier facing the lateral edge of the diaper is formed by the respective lateral zone 19 of the continuous upper layer 5, while the two sides facing the longitudinal axis AA' are formed by the central zone 20 of the said layer 5.

According to the present invention the continuous upper layer 5 which forms the two elasticated flaps 11 is made of a sheet of material which is permeable at the central zone 20 and impermeable at both lateral zones 19.

Figure 4:
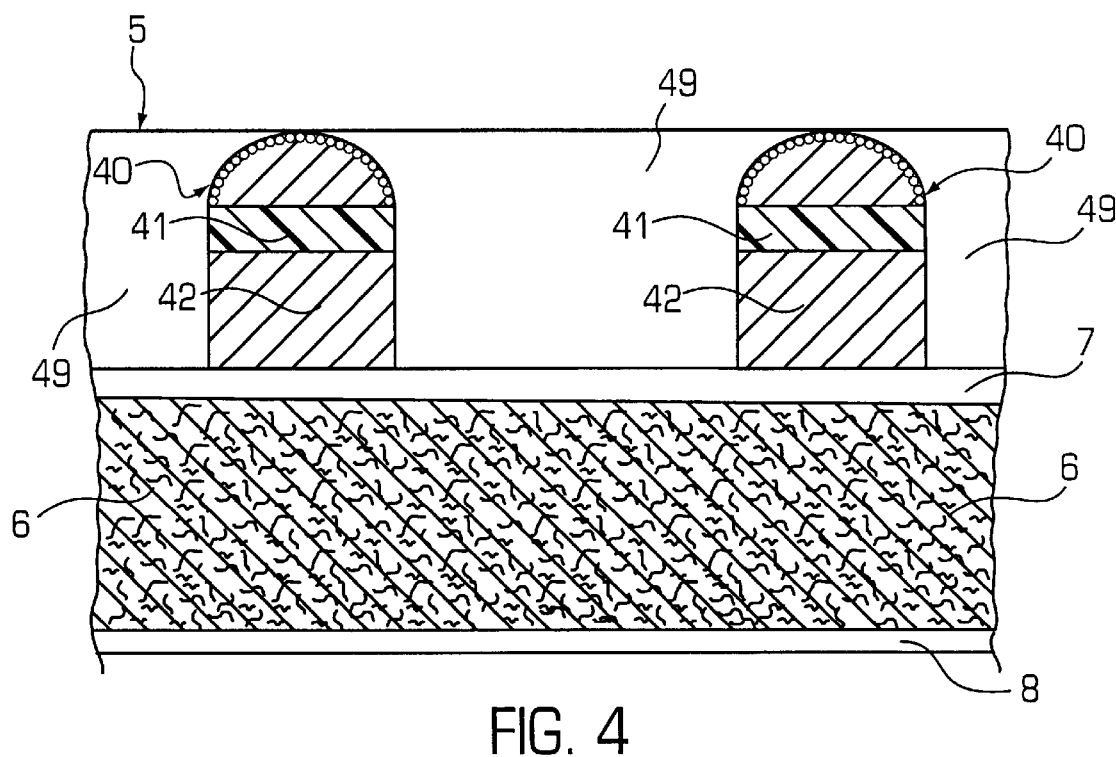
FIG. 4 is a partial sectional view similar to FIG. 2, showing a modified construction.

The use is particularly preferred of the covering structure for sanitary products described in U.S. Pat. No. 4,780,352 held by the present applicant. The structure disclosed in U.S. Pat. No. 4,780,352 and shown in FIG. 4 of the present application is perforated and includes an outer layer 40, designed to come into direct contact with the user's skin and made of a hydrophobic fibre non-woven fabric, an intermediate layer 41 consisting of a plastics sheet or film of hydrophobic material and an inner layer 42 designed to face into the absorbent article and made of a hydrophobic fibre nonwoven fabric; the three layers are joined to form a structure having a thickness between 200 microns and 700 microns. The three layers are perforated by holes 49 in the central zone 20 and are imperforate in the lateral zones 19.

According to the present invention, the continuous upper layer 5 of the diaper 1 consists of a covering structure of the type described that has been perforated, and therefore made liquid-permeable, only at the central zone 20, leaving the two lateral zones 19 imperforate and therefore impermeable.

Each flap 11 is therefore able, in use, to form a barrier characterised by a side facing the longitudinal axis AA' of the diaper 1 which is liquid permeable like all the central zone 20 of the continuous upper layer 5, and an impermeable side facing the lateral edge of the diaper 1, thereby obtaining improved containment of lateral leakage both of liquids and of solid excrement, with a simplified structure not requiring additional treatment or material.

It is also possible, without departing from the scope of the present invention, to use as the continuous upper layer 5 a perforated structure of the type described in which the upper layer of non-woven fabric is made of hydrophobic fibres made slightly hydrophilic; this increases the speed with which liquids pass to the underlying absorbent element 6 at the permeable central zone 20.

Figure 3:
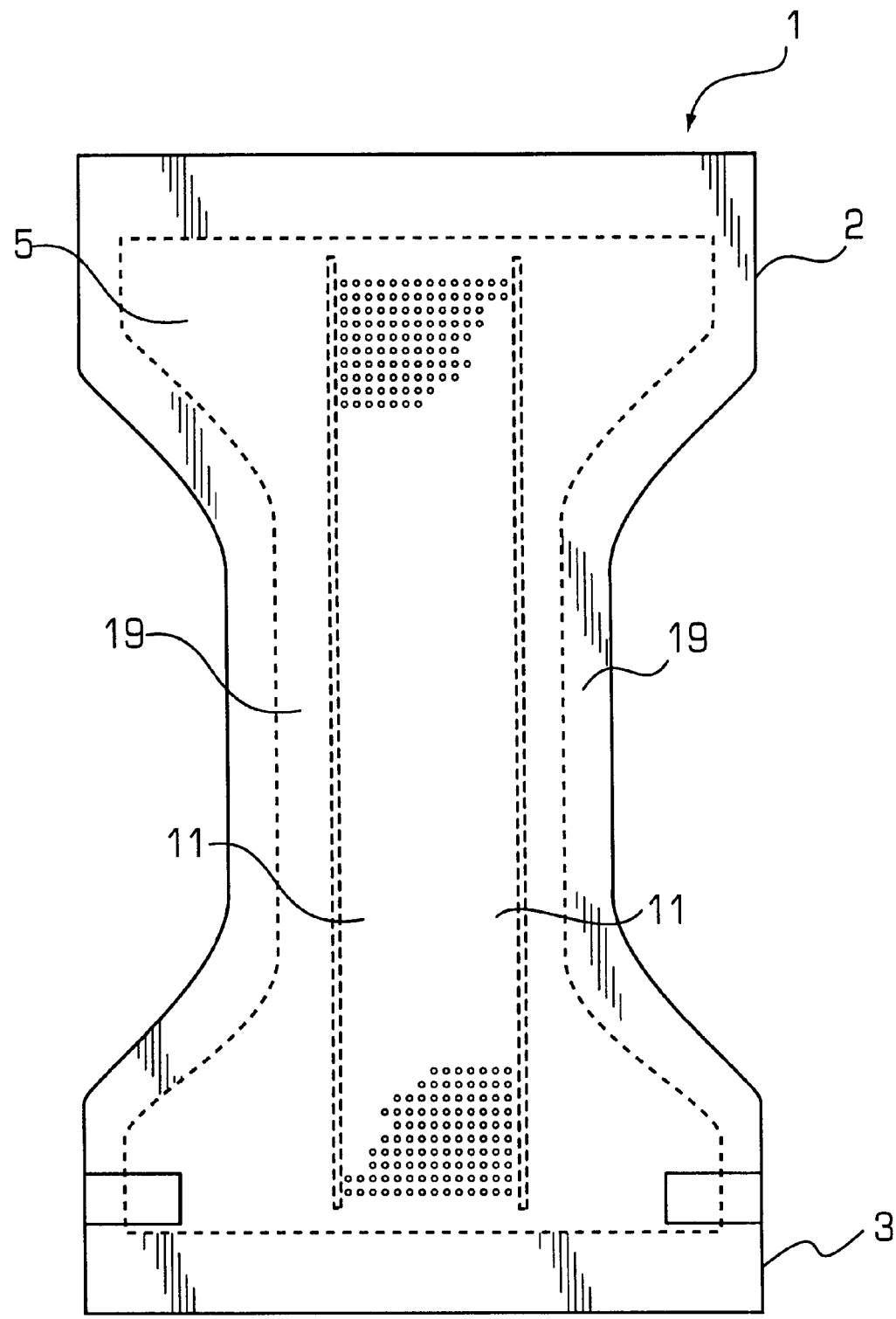
FIG. 3 is a plan view of a different configuration of a disposable diaper according to the present invention.

In an alternative configuration, shown in FIG. 3, the diaper 1 with elasticated flaps 11 is characterised by a continuous upper layer 5 which is not perforated both at the two lateral zones 19 and at the front and rear regions 2, 3.

The two non-perforated zones at regions 2, 3 act as barrier elements against leaks which, under certain conditions, can occur at the respective ends of the absorbent element 6 owing to flow-back of previously absorbed liquid.

This gives the further advantage of sealing the areas at the user's waist against moisture, using a structure characterised by the same manufacturing simplicity and without the need for additional elements such as, for example, the impermeable strips generally positioned under the upper permeable layer at the two ends of the diaper.

In a further alternative configuration, the elastic elements of the elasticated flaps are fixed for substantially the entire length i the inner surface of the continuous upper layer and at either end, situated at the front and rear end of the diaper respectively, are also fixed to the lower tissue layer covering the absorbent element, by fixing elements made, for example, of adhesive.

Naturally, the principle of the invention remaining the same, the details can be widely varied with respect to those described and illustrated without thereby departing from the scope of the present invention.

What is claimed is:

1. An absorbent article having a length longer than a width thereof including a continuous single sheet upper layer (5) extending the entire length and width of the article, a lower liquid-impermeable layer (9) coextensive with said upper layer and an absorbent element (6) interposed between the upper layer (5) and the lower layer (9), said upper layer (5) forming tow elasticated flaps (11) extending alongside each other generally longitudinally of the absorbent article and completely overlying the absorbent element, wherein the upper layer (5) has a liquid-permeable central zone (20) between the two flaps (11) and two liquid-impermeable lateral zones (19) outwardly of the two flaps (11), and the two flaps (11) are elasticated by use of elastic elements (14) each elastic element being spaced inwardly from opposite edges of said absorbent element respectively and straddling the central zone (20) and one of the lateral zones (19).

2. An article according to claim 1, characterised in that the central zone (20) is perforated.

3. An article according to claim 1 characterised in that the lateral zones (19) are substantially free of perforations.

4. An article according to claim 1 characterised in that it includes elastic parts (10) extending generally parallel to the two flaps (11) along the lateral edges of the absorbent element.

5. An article according to claim 1, characterised in that the elastic elements (14) are glued to the upper layer 5 along most of their length.

6. An article according to claim 5, characterized in that the elastic elements (14) each comprise only one elastic element formed by a rubber strip.

7. An article according to claim 5, characterised in that the elastic elements (14) each comprise two or more elastic members, preferably threads.

8. An article according to claim 1, characterised in that the upper layer (5) is impermeable at the longitudinal end zones of the article.

9. An absorbent article according to claim 1, in the form of a disposable diaper.

10. An absorbent article having a length longer than a width thereof including a continuous single sheet upper layer (5) extending the entire length and width of the article, a lower liquid-impermeable layer (9) coextensive with said upper layer and an absorbent element (6) interposed between the upper layer (5) and the lower layer (9), said upper layer (5) forming tow elasticated flaps (11) extending alongside each other generally longitudinally of the absorbent article and completely overlying the absorbent element, wherein the upper layer (5) has a liquid-permeable central zone (20) between the two flaps (11) and two liquid-impermeable lateral zones (19) outwardly of the two flaps (11), and the two flaps (11) are elasticated by use of elastic elements (14), each elastic element being spaced inwardly from opposite edges of said absorbing element respectively and straddling the central zone (20) and one of the lateral zones (19), wherein the upper layer (5) comprises:

an outer layer, designed to come into contact with the user's skin, made of non-woven fabric constituted of hydrophobic fibres, an intermediate layer comprising a film of impermeable hydrophobic material, and an inner layer made of non-woven fabric constituted of hydrophobic fibres, and in that the upper layer (5) is perforated through the three above layers in the central zone (20) but imperforate in the two lateral zones (19).

11. An article according to claim 10, wherein at least the outer layer of the upper layer (5), intended to come into contact with the user's skin, is treated with hydrophilizing agents.

* * * * *